United States Patent [19]

Eisenberg

[11] 4,152,271
[45] May 1, 1979

[54] TRACER-CONTAINING COMPOSITION

[75] Inventor: Sylvan Eisenberg, San Francisco, Calif.

[73] Assignee: Micro Tracers, Inc., San Francisco, Calif.

[21] Appl. No.: 437,037

[22] Filed: Jan. 28, 1974

Related U.S. Application Data

[63] Continuation of Ser. No. 280,064, Aug. 11, 1973, abandoned.

[51] Int. Cl.² .............. A23K 1/175; C09K 3/00
[52] U.S. Cl. .................... 252/1; 252/408; 426/74; 426/96; 426/97
[58] Field of Search .............. 324/41, 43 R; 252/1, 252/408; 426/74, 96, 97; 102/70 R

[56] References Cited

U.S. PATENT DOCUMENTS

| | | | |
|---|---|---|---|
| 2,868,644 | 1/1959 | Eisenberg | 426/74 |
| 2,928,739 | 6/1958 | Harrel | 426/74 |
| 3,139,528 | 6/1964 | Henderson et al. | 324/34 |
| 3,233,173 | 2/1966 | Lees et al. | 324/61 |
| 3,469,990 | 9/1969 | Eisenberg | 426/74 |

*Primary Examiner*—Leland A. Sebastian

[57] ABSTRACT

A dry homogeneous admixture including a bulk material, a micro-ingredient, and a solid particulate tracer in a preselected ratio to the micro-ingredient, comprising a vehicle of ground iron or other ferromagnetic material that will become magnetized by a magnetic field, but loses its magnetism in the absence of such a field. The vehicle itself serves as the tracer when used with magnetic detection techniques. Additional tracers are provided by coating the vehicle with detectable coatings such as dyes.

1 Claim, No Drawings

TRACER-CONTAINING COMPOSITION

RELATED APPLICATIONS:

This application is a continuation of my co-pending application, Ser. No. 280,064, filed Aug. 11, 1973, now abandoned for TRACERS.

This invention relates to the same art as applicant's prior U.S. Pat. Nos. 2,868,644 and 3,469,990. The tracers of this invention differ from those of the prior art in that the vehicle comprises a ground soft iron or other ferromagnetic material. Thus, by employing magnetic detection techniques, the vehicle itself may serve as a tracer.

An advantage of the tracer of the present invention is that it can be separated from a mix much faster and easier than prior tracers by means of a magnetic probe.

Another advantage of the tracer of the present invention is that it may be separated from a mix by means of a magnetic probe from either a sample of mix, or a moving stream of mix, conveyed during production.

A further advantage of the present invention is that it permits examination of large samples of mix, avoiding the restriction to small samples required when sedimentation separation procedures must be employed.

A series of such vehicle tracers can be made by using iron alloys or other ferromagnetic materials distinguishable from each other by chemical or physical means.

An additional series of tracers can be made from any one vehicle by coating the vehicle with a number of distinguishable coatings. Certified FD&C dyes may be used as identifiable coating materials. Also, mixtures of dyes differing in diffusion rates may be used to increase the number of tracers, and to produce truly unique markers.

In animal feed applications, essential nutrients or drugs may themselves be used as identifiable coatings.

The vehicle for the tracer of the present invention is ground soft iron or some other ferromagnetic material that can be magnetized by a magnetic field, but that will lose its magnetism in the absence of such a field. The particulate ferromagnetic material passes a U.S. 20 mesh screen but is retained by a U.S. 325 mesh screen. The vehicle should be as closely classified in particle size as practical; for example, passing a U.S. 35 mesh screen but retained by a U.S. 80 mesh screen. Finer or coarser ranges may be preferred depending upon the nature of the dry mix to be marked with the tracer.

Coated tracers may be produced by first dry-blending 0.1% to 5% by weight of water soluble FD&C colors with the particulate ferromagnetic vehicle. Water is then added to the dye mixture to dissolve the dye and then mixing is continued. The mix is then dried, and screened. The portion of the dry mix passing U.S. 35 mesh screen but retained by U.S. 80 mesh screen is packaged as the finished product. The screening may be varied depending upon application.

Certified FD&C dyes such as Blue #1, Red #2, Violet #1 and Yellow #6 serve as easily identifiable coating materials. Mixtures of dyes differing in diffusion rates may be used to increase the number of different tracers and to produce truly unique markers. For example mixtures of Blue #1 and Yellow #6 produce blue streaks or rings with yellow nuclei by the detection procedure described hereinbelow. Mixtures of Blue #1 and Red #2 produce blue streaks or rings with red nuclei.

The tracer of the present invention finds particular application in use with animal feeds. The iron vehicle coated tracer will be of such particle size that there will be roughly 20,000 particles per gram. The tracer is pre-mixed with a micro-ingredient which is ordinarily difficult to identify. The tracer is included in the pre-mix at such a level as to contribute 5.0 grams of tracer per ton of completed feed. At this level 80 gram samples of the completed feed will contain approximately 9 tracer particles, which is the minimum number desired per assay on a statistical ground. The pre-mix is then mixed with the feed. Thus samples of the final feed mix contain both micro-ingredient and tracer.

Detection of the tracer in samples of finished feed may be easily achieved by means of a magnetic probe. Alternatively, the tracer may be detected in a moving stream of feed by means of a magnetic probe.

A preferred method for detection of the tracer in samples of finished feed involves use of the following materials and steps Materials:
1. Filter paper, 7.0 cm. circles, Whitman #1, or any other.
2. A 1-pint mason jar.
3. A tablespoon, a small measuring cup, or a scale suitable for dispensing 3 ounces of completed feed.
4. A blender (Osterizer or equivalent) for grinding pellets, preferably suitable for use with mason jars.
5. A special magnetic cap for a mason jar, one form of which is essentially as follows. The threaded ring of a standard 2-part mason jar cap is cemented to the active face of a 3-inch diameter magnet such as is used in permanent magnet radio speakers. The active face of this magnet exposes an approximately 1-inch diameter pole by an approximately 1/16-inch gap. The magnetic field in the way of this gap is intense compared to other areas. A sheet of 7.0 cm. filter paper just fits within the threaded ring, and when inserted it lies flat against the active face of the magnet.
6. A 2-4 oz. dropping bottle containing 90% ethyl alcohol, 90% propyl alcohol or methanol; or water if other solvents are unavailable.

Procedure:
1. Transfer 3 oz. of mash (or of pellets previously ground to pass a 30 mesh screen) into the mason jar.
2. Insert filter paper into magnetic cap.
3. Close mason jar with cap, and shake jar for 30 to 60 seconds maximizing contact of all parts of sample with magnetic cap.
4. Remove cap, and invert it so that filter paper is on top and horizontal.
5. Put 8-10 drops of solvent on center of paper. Permit solvent to slowly diffuse outward so that it wets material retained in the way of the circular magnetic gap.
6. Streaks of color will radiate outwards from each tracer particle. The color identifies the specific tracer used.
7. Remove paper from cap. After drying, dust off debris, and count spots or streaks for quantitative quality control if this is desired.
8. Like tracers of different color can be detected and/or counted concurrently.

Other modifications of this detection procedure are better designed for examining larger samples. For example, a pound or more of mash can be fed as a moving stream down a near-vertical chute with the active face of the magnet serving as part of the chute. A sheet of filter paper is clamped over the face of the magnet, and the sample is passed over the paper in a thin stream. Tracer particles are retained in the way of the circular magnetic gap, most at the top of the circle. Those not trapped at the top are trapped at the bottom. Development is done as described before. The chute is shifted to a horizontal position, and enough solvent is dropped on the center of the paper so that solvent diffuses through the paper until it reaches and goes beyond the annular magnetic gap.

The tracer of the present invention is also applicable for use in the manufacture of powdered explosives, particularly those used in the production of safety fuse. Saftey fuse contains black powder on the order of one gram per linear foot. Safety fuse having an intermittent powder train will either extinguish, or burn faster, depending upon the gap in the powder train. Either event is dangerous. Continuity of powder train in safety fuse can be monitored during production with 100% quality control by inclusion of as little as 0.2% of the coated tracer of the present invention in the powder mix any time before the powder is fed into the developing fuse sheath. With a tracer passing U.S. 35 mesh but retained by U.S. 80 mesh, this will contribute approximately 40 tracer particles per linear foot of fuse. With a like tracer, but one passing a U.S. 80 mesh screen but retained by a U.S. 150 mesh screen, the tracer would contain roughly 80,000 particles per gram, and the fuse would contain roughly 160 tracer particles per linear foot, or about 13 particles per linear inch. With a continuous powder train, chances that any given inch of fuse would have no tracer particles are less than 3 in 1000. Therefore absence of tracer particles as detected by a magnetometer or other sensor in any one inch unit of fuse would indicate a one inch or longer break in the powder train. Higher levels of tracer would permit detection of even shorter breaks. Thus safety fuse having an intermittent powder train may be detected and withheld from the market.

What is claimed is:

1. A composition of matter in the form of a generally homogeneous admixture, said admixture being comprised of a major portion of a bulk ingredient, a minor portion of a micro-ingredient, and a tracer provided in a preselected ratio with said micro-ingredient, said tracer comprising a finely divided ferromagnetic material having a particle size of from about 20 to about 325 mesh.

* * * * *